(12) United States Patent
Liu et al.

(10) Patent No.: US 9,169,171 B2
(45) Date of Patent: Oct. 27, 2015

(54) AROMATIZATION OF METHANE WITH COMBINATION OF CATALYSTS

(71) Applicants: Agency for Science, Technology and Research, Singapore (SG); Mitsui Chemicals Inc., Tokyo (JP)

(72) Inventors: Yan Liu, Jurong Island (SG); Armando Borgna, Jurong Island (SG)

(73) Assignees: Agency for Science, Technology and Research, Singapore (SG); Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 13/624,489

(22) Filed: Sep. 21, 2012

(65) Prior Publication Data

US 2013/0116493 A1     May 9, 2013

Related U.S. Application Data

(60) Provisional application No. 61/537,232, filed on Sep. 21, 2011.

(51) Int. Cl.
 *C07C 2/76* (2006.01)
 *C07C 2/00* (2006.01)
(52) U.S. Cl.
 CPC ............... *C07C 2/76* (2013.01); *C07C 2529/48* (2013.01); *C07C 2529/78* (2013.01)
(58) Field of Classification Search
 USPC .................................................. 585/415, 417
 See application file for complete search history.

(56) References Cited

U.S. PATENT DOCUMENTS

| | | | |
|---|---|---|---|
| 4,139,600 A | 2/1979 | Rollmann et al. | |
| 4,954,325 A | 9/1990 | Rubin et al. | |
| 6,239,057 B1 | 5/2001 | Ichikawa et al. | |
| 6,552,243 B2 | 4/2003 | Allison et al. | |
| 8,021,643 B2 | 9/2011 | Lai et al. | |
| 2008/0293980 A1* | 11/2008 | Kiesslich et al. | 585/408 |
| 2009/0240093 A1* | 9/2009 | Ichikawa et al. | 585/315 |
| 2010/0285948 A1 | 11/2010 | Liu et al. | |

FOREIGN PATENT DOCUMENTS

| | | |
|---|---|---|
| WO | 2009/091336 A1 | 7/2009 |
| WO | 2009140790 A1 | 11/2009 |

OTHER PUBLICATIONS

Shu et al., Methane dehydro-aromatization over Mo/MCM-22 catalysts: a highly selective catalyst for the formation of benzene, 2000, Catalysis Letters, vol. 70, pp. 67-73.*

(Continued)

*Primary Examiner* — In Suk Bullock
*Assistant Examiner* — Youngsul Jeong
(74) *Attorney, Agent, or Firm* — Wolf, Greenfield & Sacks, P.C.

(57) ABSTRACT

A heated reaction gas comprising methane is contacted with first and second catalysts to catalyze production of an aromatic hydrocarbon. The first catalyst is more active than the second catalyst for catalyzing aromatization of methane, and the second catalyst is more active than the first catalyst for catalyzing aromatization of ethane. A reactor for producing aromatic hydrocarbons from the reaction gas may have a conduit defining a reaction zone for the reaction gas to react therein, and the first and second catalysts may be disposed in the reaction zone.

8 Claims, 3 Drawing Sheets

(56) References Cited

OTHER PUBLICATIONS

Smieskova et al., Aromatization of methane on Mo modified zeolites: Influence of the surface and structural properties of the carriers. Applied Catalysis A: General. Jan. 20, 2010;377:83-91.

Chu et al., A feasible way to enhance effectively the catalytic performance of methane dehydroaromatization. Catalysis Communications. Dec. 6, 2010;11:513-7.

Skutil et al., Some technological aspects of methane aromatization (direct and via oxidative coupling). Fuel Processing Technology. 2006;87:511-21.

Liu et al., Methane dehydroaromatization under nonoxidative conditions over Mo/HZSM-5 catalysts: Identification and preparation of the Mo active species. Journal of Catalysis. Mar. 24, 2006;239:441-50.

Ha et al., Aromatization of methane over zeolite supported molybdenum: active sites and reaction mechanism. Journal of Molecular Catalysis A: Chemical. 2002;181;283-90.

Shu et al., Methane dehydro-aromatization over Mo/MCM-22 catalysts: highly selective catalyst for the formation of benzene. Catalysis Letters. 2000;70:67-73.

Xu et al., Recent advances in methane dehydro-aromatization over transition metal ion-modified zeolite catalysts under non-oxidative conditions. Applied Catalysis A: General. 1999;188:53-67.

Huang et al., Structure and acidity of Mo/H-MCM-22 catalysts studied by NMR spectroscopy. Catalysis Today. 2004;97:25-34.

Chu et al., Dehydroaromatization of methane with a small amount of ethane for higher yield of benzene. Chinese Chemical Letters. 2004;15(5):591-3.

Intellectual Property Office of Singapore, "Invitation to Respond to Written Opinion", dated Nov. 7, 2013, in related Singapore Patent Application No. 201207026-4.

Second Written Opinion mailed Jul. 1, 2014 for Singaporean Application No. SG201207026-4.

\* cited by examiner

AROMATIZATION OF METHANE WITH COMBINATION OF CATALYSTS

CROSS-REFERENCE TO RELATED APPLICATION

This application claims the benefit of, and priority from, U.S. Patent Application Ser. No. 61/537,232, filed Sep. 21, 2011, and entitled "PROCESS FOR PRODUCTION OF AROMATIC HYDROCARBONS FROM NATURAL GAS," the entire contents of which are incorporated herein by reference.

FIELD

The present invention relates, in some aspects, to processes and systems for aromatization of low hydrocarbons, including production of aromatic hydrocarbons from natural gas.

BACKGROUND

It is known that dehydroaromatization of methane ($CH_4$) under non-oxidative conditions is thermodynamically more favorable to aromatics than to olefins, and molybdenum-modified zeolites or aluminosilicates such as Mo/ZSM-5 and Mo/MCM-22 are found to be effective catalysts for such reactions. Extensive research on the performance of such catalysts has been conducted and reported, and it has been found that the production performance depends on the structure and composition of the catalyst tested and how the catalyst is activated. Thus, research reported to date has focused on identifying a catalyst that can be activated to provide improved aromatization performance such as benzene yield from methane aromatization.

Representative publications of such research results include:

Smieskova et al. "Aromatization of methane on Mo modified zeolites: Influence of the surface and structural properties of the carriers," *Applied Catalysis A: General*, 2010, vol. 377, pp. 83-91;

Skutil et al., "Some technological aspects of methane aromatization (direct and via oxidative coupling)," *Fuel Processing Technology*, 2006, vol. 87, pp. 511-51;

Liu et al., "Methane dehydroaromatization under nonoxidative conditions over Mo/HZSM-5 catalysts: Identification and preparation of the Mo active species," *Journal of Catalysis*, 2006, vol. 239, pp. 441-450;

Ha et al., "Aromatization of methane over zeolite supported molybdenum: active sites and reaction mechanism," *Journal of Molecular Catalysis A: Chemical*, 2002, vol. 181, pp. 283-290;

Shu et al., "Methane dehydro-aromatization over Mo/MCM-22 catalysts: highly selective catalyst for the formation of benzene," *Catalysis Letters*, 2000, vol. 70, pp. 67-73;

Xu et al., "Recent advances in methane dehydro-aromatization over transition metal ion-modified zeolite catalysts under non-oxidative conditions," *Applied Catalysis A: General*, 1999, vol. 188, pp. 53-67;

Huang et al., "Structure and acidity of Mo/H-MCM-22 catalysts studied by NMR spectroscopy," *Catalysis Today*, 204, vol. 97, pp. 25-34;

Chu et al., "A feasible way to enhance effectively the catalytic performance of methane dehydroaromatization," *Catalysis Communications*, 2010, vol. 11, pp. 513-517; and Chu et al., "Dehydroaromatization of methane with a small amount of ethane for higher yield of benzene," *Chinese Chemical Letters*, 2004, vol. 15, pp. 591-593.

SUMMARY

It has been surprisingly discovered that heating simulated natural gas in the presence of a combination of different catalysts can produce aromatics with improved yield when the combination of catalysts includes a first catalyst that is more active for catalyzing aromatization of methane and a second catalyst that is more active for catalyzing aromatization of ethane. For example, the first catalyst may be a Mo/MCM-22 catalyst, and the second catalyst may be a Mo/ZSM-5 catalyst.

In accordance with an aspect of the present invention, there is provided a method in which a heated reaction gas comprising methane is contacted with a first catalyst and a second catalyst to catalyze production of an aromatic hydrocarbon. The first catalyst is more active than the second catalyst for catalyzing aromatization of methane, and the second catalyst is more active than the first catalyst for catalyzing aromatization of ethane. At least one of the first and second catalysts may be an aluminosilicate zeolite modified by a transition metal. The first catalyst may be a MCM-22 zeolite modified by a first transition metal. The second catalyst may be a ZSM-5 zeolite modified by a second transition metal. The first transition metal and second transition metal may be molybdenum. Each catalyst may comprise about 3 to about 12 wt % of molybdenum. Each catalyst may have a Si/2Al ratio of from 25 to 45. The heated reaction gas may be heated to a temperature of about 600 to about 700° C. Prior to contacting the reaction gas, the first and second catalysts may be heated to at least 300° C. in the presence of propane. The weight ratio of the first and second catalysts may be about 1:1.

In another aspect, there is provided a reactor for producing aromatic hydrocarbons from a reaction gas comprising methane. The reactor comprises a conduit defining a reaction zone for the reaction gas to react therein; and a first catalyst and a second catalyst in the reaction zone. The first catalyst is more active than the second catalyst for catalyzing aromatization of methane, and the second catalyst is more active than the first catalyst for catalyzing aromatization of ethane. At least one of the first and second catalysts may be an aluminosilicate zeolite modified by a transition metal. The first catalyst may be a MCM-22 zeolite modified by a first transition metal. The second catalyst may be a ZSM-5 zeolite modified by a second transition metal. The first transition metal and second transition metal may be molybdenum. Each catalyst may comprise about 3 to about 12 wt % of molybdenum. Each catalyst may have a Si/2Al ratio of from 25 to 45. The weight ratio of the first and second catalysts may be about 1:1.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
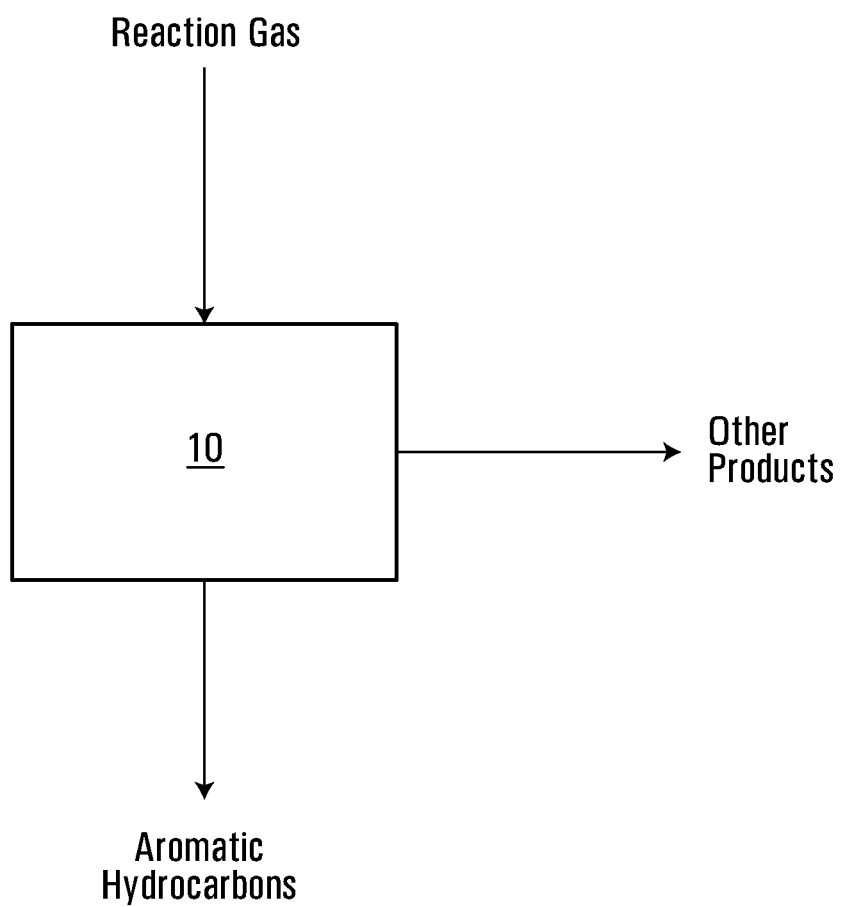
FIG. 1 is a schematic diagram of an aromatization process using a reactor, exemplary of an embodiment of the present invention.

A process for producing aromatic hydrocarbons from a reaction gas containing methane according to selected embodiments of the present invention is illustrated in FIG. 1. As shown, the reaction gas is fed to a reactor 10, in which the reaction gas may be heated under non-oxidative conditions to produce aromatic hydrocarbons and other products such as hydrogen.

The reaction gas may be a natural gas. Typical natural gases may include, e.g. 75 to 99 mol % of methane ($CH_4$), 0.01 to 15 mol % of ethane ($C_2H_6$), 0.01 to 10 mol % of propane ($C_3H_8$), up to 0.30 mol % of carbon dioxide ($CO_2$), and other minor components. The reaction gas may also be any other synthesized or naturally existing gases or mixtures of gases that contain low carbon alkanes, or other low carbon aliphatic hydrocarbons, such as $C_1$-$C_4$ hydrocarbons.

The actual reactions occurring in reactor 10 may be complicated and may vary in different embodiments depending on various factors as can be understood by those skilled in the art. In many instances, the complete reaction mechanisms may not be completely understood. However, the overall reactions may include a reaction result that can be described as:

$$6CH_4 = 9H_2 + C_6H_6. \quad (1)$$

In selected embodiments, ethane is also expected to be present in reactor 10. Ethane may be included in the input gases such as the reaction gas, or may be formed in reactor 10. As such, the overall performance of the aromatization process can be enhanced by including in reactor 10 a combination of catalysts where a first catalyst is more active for catalyzing aromatization of methane and a second catalyst is more active for catalyzing aromatization of ethane. A catalyst is more active if it provides a higher yield of the desired product, or if it has a longer lifetime as an active catalyst for the desired reaction without reactivation, or both.

Figure 2:
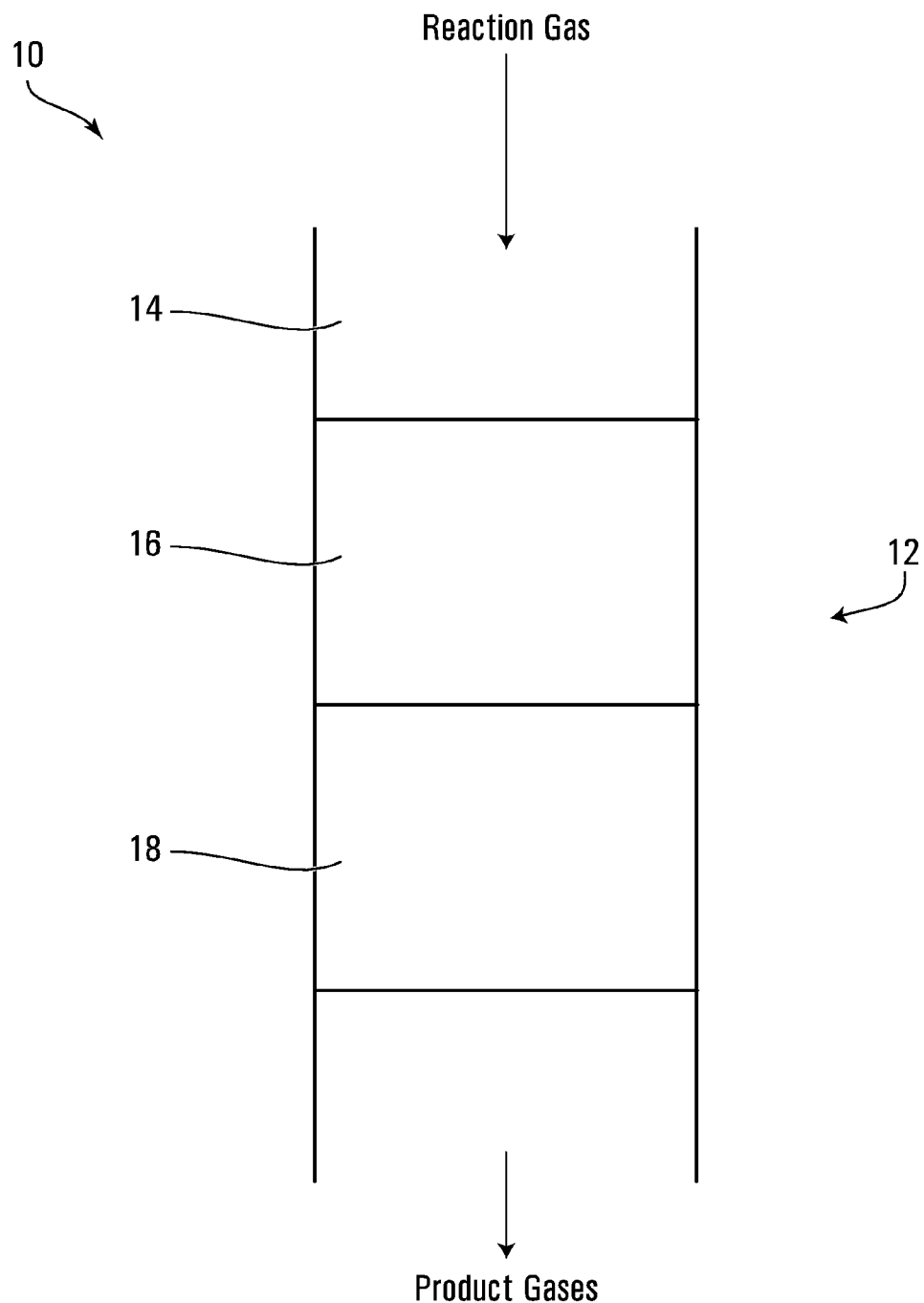
FIG. 2 is a schematic sectional view of a reaction zone of the reactor of FIG. 1.

The catalysts may be placed in a catalyst bed 12 as illustrated in FIG. 2 (not separately shown in FIG. 1). As depicted in FIG. 2, catalyst bed 12 is in a conduit 14 in reactor 10, in which the reaction gas passes through and the aromatization reactions take place. The space in conduit 14 where the reaction gas contacts the catalysts and reacts is referred to as the reaction zone.

In selected embodiments, conduit 14 may be arranged vertically and the reaction gas may be flown downward as depicted in FIG. 2. Other arrangements are also possible.

At least two different types of catalysts are placed in catalyst bed 12. As depicted in FIG. 2, a first catalyst 16 is placed upstream (on top as depicted in FIG. 2) in catalyst bed 12, and a second catalyst 18 is placed downstream (at the bottom as depicted in FIG. 2) in catalyst bed 12. In selected embodiments, catalyst 16 is a Mo/MCM-22 catalyst, and catalyst 18 is a Mo/ZSM-5 catalyst. MCM-22 and ZSM-5 are each well-known aluminosilicate zeolites, and those of ordinary skill in the art will be aware of such compounds, their physical structures, and techniques for producing such structures. Other possible catalysts that can be used, their selection and preparation will be described further below. In different embodiments, the catalysts may also be arranged differently as discussed elsewhere herein.

Reactor 10, catalyst bed 12 and conduit 14 may be designed and constructed according to any suitable conventional techniques with the exception of the catalysts in catalyst bed 12 and with any possible or necessary modification in view of, or to accommodate, the combination of catalysts described herein. For example, reactor 10 may be a continuous flow reactor, and catalyst bed 12 may a fixed catalyst bed. The sizes and shapes of reactor 10, catalyst bed 12 and conduit 14 may be selected by those skilled in the art according to known techniques for designing gas phase reactors. The different components in the reactor may also be constructed using suitable materials known to those skilled in the art with the additional requirement that they be compatible with the combination of catalysts described herein Some optional and necessary components of reactor 10, and optional or necessary equipments and devices for operating reactor 10, are not depicted in the figures, but these can be readily understood and provided by those skilled in the art in view of the present disclosure.

During operation, the reaction gas is passed through catalyst bed 12 in conduit 14 at selected temperature, pressure and flow rate. The temperature, pressure, flow rate, and other operating conditions in conduit 14, are selected and controlled to provide non-oxidative dehydroaromatization conditions. As will be understood by those skilled in the art, to avoid oxidative reactions, the reactants used for the production process should be non-oxidative, and the reaction gas should not contain or contact oxidative substances such as oxidative gases.

In selected embodiments, the reaction temperature in the reaction zone may be about 650° C. and the pressure in conduit 14 may be about 0.1 MPa or about 1 atm. In some embodiments, the reaction temperature may be selected from the range of about 500 to about 900° C., such as from about 600 to about 700° C.; and the reaction pressure may be selected from the range of 0.1 to about 1 MPa, such as from about 0.1 to about 0.5 MPa.

In selected embodiments, the space velocity of the reaction gas in conduit 14 may be about $10\,h^{-1}$. In some embodiments, the space velocity of the reaction gas may be in the range of about 5 to about $15\,h^{-1}$, such as from about 7 to about $12\,h^{-1}$.

The space velocity, reaction temperature, and reaction pressure can affect the reaction results and process performance, and thus may be selected to optimize certain aspects of the reaction process for a given application.

As a result of the reactions that occur in reactor 10, aromatic hydrocarbons and other products such as hydrogen gas are produced. Possible aromatic hydrocarbons produced in reactor 10 include benzene, toluene, xylene, naphthalene, ethylbenzene, styrene, or mixtures thereof. In particular, the reaction conditions may be optimized to produce one or more of benzene, toluene, and xylene in selected embodiments.

Conveniently, when a combination of different catalysts as described herein is provided and present in reactor 10, improved processing performance may be obtained, as compared to a process using only one of the catalysts.

For example, it has been found that Mo/ZSM-5 is very efficient for catalyzing ethane aromatization reaction. Tests show that when only Mo/ZSM-5 was used, 100% ethane conversion could be obtained for a long time with stable benzene yield. However, the benzene yield decreased quickly when the catalyst was becoming deactivated. By comparison, Mo/MCM-22 has been found to be more efficient for methane aromatization reaction. When only Mo/MCM-22 was used, the benzene yield could be maintained at a relatively high level for a certain period of time, but this catalyst exhibited low activity for ethane aromatization reaction.

Tests have shown that when the combination of a Mo/ZSM-5 catalyst and a Mo/MCM-22 catalyst was used for natural gas aromatization reaction, the conversion performance from both ethane and methane to benzene, toluene and xylene products could be improved or maximized, as compared to using any one of these catalysts.

Without being limited to any specific theory, it is believed that Mo/MCM-22 can efficiently convert methane to aromatics. During this conversion, some ethane may be produced. The produced or unreacted (if present in the input reaction gas) ethane can be efficiently converted to aromatics when it is in contact with Mo/ZSM-5. As a result, the overall performance of the process can be enhanced. Test results indicated that both benzene yield and catalytic stability could be increased when both Mo/ZSM-5 and Mo/MCM-22 were used.

With an embodiment of the present invention, the benzene yield can be expected to increase by 30% over a 150 h processing period, as compared to a conventional process for non-oxidative dehydroaromatization of methane using one type of catalyst.

As can be understood, similar results or improvement could be expected if Mo/MCM-22 is replaced with another catalyst that is more efficient or active for catalyzing methane aromatization, and Mo/ZSM-5 is replaced with another catalyst that is more efficient or active for catalyzing ethane aromatization. For example, other catalysts that have a zeolite structure with pore channel sizes similar to those of MCM-22 or ZSM-5 may be suitable catalysts in selected embodiments. Suitable catalysts may have different pore structures that are similar to those of MCM-22 or ZSM-5 respectively. Different pore structures may be selected based on their effects on catalytic activity. In some embodiments, the catalysts may have Mo-loading of about 1% to about 15%, and Si/2Al ratio of 25 to 45.

In view of the discussion above, the catalysts in catalyst bed 12 may be arranged to optimize the performance, such as by arranging the catalysts in a way that the reaction gas first comes into contact with catalyst 16 and then comes into contact with catalyst 18.

However, in some embodiments, improved performance could still be obtained if the reaction gas, such as natural gas, first comes into contact with catalyst 18 and then comes into contact with catalyst 16.

In selected embodiments, catalysts 16 and 18 may be pre-mixed and the mixture may be placed in catalyst bed 12, without a separation section for each catalyst.

In any of the aforementioned arrangements, the weight ratio of catalyst 16 and catalyst 18 may be about 1:1, or may be of another value such as from 1:10 to 10:1. The ratio may be selected to optimize certain aspects of the reaction performance or for other considerations for a given application.

To activate the catalysts and improve performance, the catalysts may be subjected to pre-treatment before passing the reaction gas through conduit 14. For example, in some embodiments, the catalysts may be heated in the presence of propane at a temperature of at least 300° C., such as from 450° C. to 650° C., or from 475° C. to 525° C. The pre-treatment may last from about 10 to 100 minutes, such as about 20 to 40 minutes. The catalysts may be prepared and pre-treated as described in WO 2009/091336 to Liu et al., published Jul. 23, 2009, the entire contents of which are incorporated herein by reference. A Mo/MCM-22 catalyst may also be prepared as described in the Examples below.

The catalysts may be regenerated after deactivation, such as by an oxidation process to remove coke deposits. Regeneration of deactivated catalysts may be useful and can reduce costs in some commercial applications.

As now can be understood, in different embodiments each of catalysts 16 and 18 may be an aluminosilicate zeolite modified by a transition metal. The zeolite for the first catalyst (catalyst 16) may be based on MCM-22 zeolite. The zeolite for the second catalyst (catalyst 18) may be based on ZSM-5 zeolite. It is noted that in the literature MCM-22 is sometimes referred to as HMCM-22 or H-MCM-22, and ZSM-5 is sometimes referred to as H-ZSM-5 or HZSM-5. The zeolite for the first catalyst may also be another zeolite that has an MWW type framework, and the zeolite for the second catalyst may be another zeolite that has an MFI type framework. For example, the catalysts, aluminosilicates, zeolites and metal modifiers described in WO 2009/091336 may be suitable candidates for selection. Particular combinations of the different components described therein may be selected and used depending on the particular application In particular, a suitable transition metal may be molybdenum. In some embodiments, molybdenum may provide better performance than other metals. In some embodiments, tungsten or rhenium may be used. Other non-limiting examples of transition metals include, but are not limited to Sc, Ti, V, Cr, Mn, Fe, Co, Ni Cu, Zn, Y, Zr, Nb, Tc, Ru Rh, Pd, Ag, Cd, Hf, Ta, W, Re, Os, Ir, Pt, Au, Hg, a lanthanide, or an actinide, The loading of the metal in the zeolite may be selected to optimize production performance. For example, when Mo is used, its loading may be from about 1 wt % to 15%, such as about 3 wt % to about 12 wt %.

One or both of the catalysts may have a Si/2Al ratio of from 10 to 100, such as 25 to 45. In some embodiments, this ratio may be about 30 or about 35. The ratio may be selected to provide the desired acidity.

Conventional techniques for preparation of different zeolites and catalysts, and for dehydroaromatization of methane and other alkanes, may be modified or adapted by those skilled in the art in view of the present disclosure for use in some embodiments of the present disclosure. Some of such techniques are disclosed in the references listed in the Background section, and in the following references: U.S. Pat. No. 4,139,600 to Rollman et al., published Feb. 13, 1979; U.S. Pat. No. 4,954,325 to Rubin et al.; U.S. Pat. No. 6,239,057 to Ichikawa et al., issued May 29, 2001; U.S. Pat. No. 6,552,243 to Allison et al., issued Apr. 22, 2003; and U.S. 2011/0038789 to Lai et al., published Feb. 17, 2011, the entire contents of each of which are incorporated herein by reference.

It should be understood that the specific embodiments described herein are for illustration purposes. Various modifications to these embodiments are possible and may be apparent to those skilled in the art.

Some embodiments of the invention are further illustrated with the following non-limiting examples.

EXAMPLES

For the following examples, Mo/ZSM-5 and Mo/MCM-22 were prepared by impregnating ZSM-5 and MCM-22 zeolites respectively, according to conventional impregnation techniques.

ZSM-5 was obtained commercially from Zeolyst, with Si/2Al ratio of about 30.

MCM-22 with Si/2Al ratio of about 35 was prepared as follows. Sodium hydroxide (0.18 g), sodium aluminate anhydrous (0.20 g), and distilled water (27.60 g) were mixed in a mixture until dissolution. Hexamethyleneimine (HMI, 1.73 g) was added to the mixture and the resulting mixture was stirred for about 10 min. Ludox HS-40 colloidal silica (5.25 g) and MCM-22 seed (0.04 g) were added and the final mixture (35 ml) was stirred for 4 h at room temperature. Gel was formed from the mixture and was moved to an autoclave, and was heated in a Parr-Reactor (oven) at 150° C. (30 rpm) for 14 days. The product was filtered and dispersed in water until the pH of the filtrate was no greater than 9.

The catalysts were pre-treated (activated) according to the processes described in WO 2009/091336 to Liu et al., the entire contents of which are incorporated herein by reference.

In the natural gas used, the main component was methane. The natural gas also contained small amounts of $C_2$, $C_3$, and $C_4$ hydrocarbons and $CO_2$, and trace amount of $C_5$ and $C_6$ hydrocarbons.

Example I

Natural gas was used as the reaction gas and was passed through a catalyst bed as illustrated in FIG. 2. Mo/ZSM-5 was placed at the bottom of the catalyst bed (i.e. downstream in the gas flow path) and an equal amount of Mo/MCM-22 was placed on top of Mo/ZSM-5 in the catalyst bed (i.e. upstream in the gas flow path).

The reaction conditions were maintained at a temperature of about 650° C., a pressure of about 0.1 MPa, and a flow rate of the natural gas of about 7.5 ml/min. No oxidative gases were included in the reaction gases to provide non-oxidative conditions.

Figure 3:
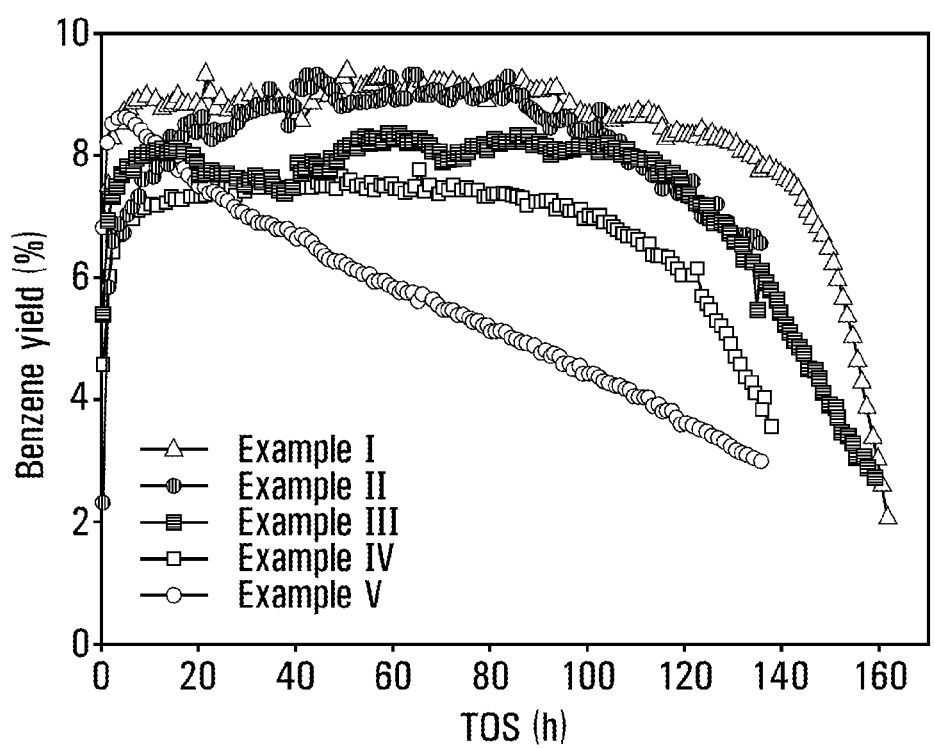
FIG. 3 is a data graph showing representative production results in example aromatization processes with different configurations of catalysts.

Representative production results are shown in FIG. 3 (marked as "Example I").

Example II

In this example, the reaction gas, catalysts used and reaction conditions were the same as in Example I, except that in the catalyst bed, Mo/ZSM-5 was placed on top (upstream) and Mo/MCM-22 was placed at the bottom (downstream).

Representative production results are shown in FIG. 3 (marked as "Example II").

Example III

In this example, the reaction gas, catalysts used and reaction conditions were the same as in Example I, except that in the catalyst bed, Mo/ZSM-5 and Mo/MCM-22 were mixed with one another. Thus, the reaction gas came into contact with the two catalysts at about the same location in the flow path.

Representative production results are shown in FIG. 3 (marked as "Example III").

Example IV (Comparative)

In this example, the reaction gas and reaction conditions were the same as in Example I. However, only Mo/ZSM-5 was placed in the catalyst bed and used as the catalyst.

Representative production results are shown in FIG. 3 (marked as "Example IV").

Example V (Comparative)

In this example, the reaction gas and reaction conditions were the same as in Example I. However, only Mo/MCM-22 was placed in the catalyst bed and used as the catalyst.

Representative production results are shown in FIG. 3 (marked as "Example V").

As can be seen from FIG. 3, the benzene yield and catalyst life were both higher when a combination of Mo/MCM-22 and Mo/ZSM-5 was used as the catalysts. Example I (Mo/MCM-22 upstream and Mo/ZSM-5 downstream) provided the highest benzene yield and catalytic life (see data points represented by triangles in FIG. 3). It was expected that at 650° C., Mo/MCM-22 initially efficiently converted methane in the natural gas to benzene and ethane; and the produced ethane and the unconverted ethane in the natural gas are then efficiently converted to benzene by the Mo/ZSM-5 catalyst downstream. While performance was also improved in Examples II and III as compared to Examples IV and V, the improvement was not as pronounced as in Example I.

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A method comprising:
   contacting a heated reaction gas comprising methane with a first catalyst and a second catalyst to catalyze production of an aromatic hydrocarbon,
   wherein said first catalyst is more active than said second catalyst for catalyzing aromatization of methane, and said second catalyst is more active than said first catalyst for catalyzing aromatization of ethane, and
   wherein said heated reaction gas initially contacts said first catalyst before contacting said second catalyst, wherein said first catalyst is a MCM-22 zeolite modified by molybdenum, and said second catalyst is a ZSM-5 zeolite modified by molybdenum, and wherein said aromatic hydrocarbon comprises benzene.

2. The method of claim 1, wherein each one of said first and second catalysts comprises about 3 to about 12 wt % of molybdenum.

3. The method of claim 1, wherein each one of said first and second catalysts has a Si/2Al ratio of from 25 to 45.

4. The method of claim 1, wherein said heated reaction gas is heated to a temperature of about 600 to about 700° C.

5. The method of claim 1, wherein, prior to said contacting, said first and second catalysts are heated to at least 300° C. in the presence of propane.

6. The method of claim 1, wherein a weight ratio of said first and second catalysts is about 1:1.

7. The method of claim 1, wherein said first catalyst is in an upstream reaction zone, and said second catalyst is in a downstream reaction zone.

8. A method comprising:
   contacting a heated reaction gas comprising methane with a mixture of a first catalyst and a second catalyst to catalyze production of an aromatic hydrocarbon,
   wherein said first catalyst is a MCM-22 zeolite modified by molybdenum and is more active than said second catalyst for catalyzing aromatization of methane, and said second catalyst is a ZSM-5 zeolite modified by molybdenum and is more active than said first catalyst for catalyzing aromatization of ethane, said first zeolite and said second zeolite having different types of zeolite structures and pore channel sizes, wherein said aromatic hydrocarbon comprises benzene.

* * * * *